(12) United States Patent
Sibata et al.

(10) Patent No.: US 6,200,583 B1
(45) Date of Patent: *Mar. 13, 2001

US006200583B1

(54) ANTIMICROBIAL AGENTS, ANTIMICROBIAL RESIN COMPOSITIONS, AND ARTICLES HAVING ANTIMICROBIAL ACTIVITY

(75) Inventors: Masayuki Sibata; Kozaburo Hayashi; Akira Hoshino, all of Tokyo (JP)

(73) Assignee: Dainichiseika Color & Chemicals Mfg. Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/271,434

(22) Filed: Mar. 18, 1999

(30) Foreign Application Priority Data

Mar. 24, 1998 (JP) .................................................. 10-076209

(51) Int. Cl.[7] .......................... A01N 25/00; A61K 31/74; A61K 31/445
(52) U.S. Cl. ...................... 424/405; 424/78.08; 424/405; 514/315; 514/316
(58) Field of Search .................................... 514/315, 316; 424/78.08, 405

(56) References Cited

U.S. PATENT DOCUMENTS 4,769,268  *  9/1988  Burton .................................... 428/97
4,938,955  *  7/1990  Nira et al. .............................. 424/79

OTHER PUBLICATIONS

CA abstract AN: 1995:471881, 1995, Nabeya et al.*
CA abstract AN: 1996:294978, 1996, Nakamura et al.*
CA abstract AN: 1997:558103, 1997, Mishima et al.*
CAS No. 91788–83–9 registry, 2000.*

* cited by examiner

Primary Examiner—Russell Travers
Assistant Examiner—Shengiun Wang
(74) Attorney, Agent, or Firm—Oblon, Spivak, McClelland, Maier & Neustadt, P.C.

(57) ABSTRACT

Antimicrobial agents comprise 2,2,6,6-tetramethyl-4-piperidine derivatives. When added to resins, these antimicrobial agents provide antimicrobial resin compositions, which in turn provide antimicrobial articles. These antimicrobial agents provide resins, synthetic fibers or the like with not only outstanding antimicrobial activity but also excellent heat resistance, weatherability and deterioration resistance without impairing the transparency and safety of these materials.

11 Claims, No Drawings

ANTIMICROBIAL AGENTS, ANTIMICROBIAL RESIN COMPOSITIONS, AND ARTICLES HAVING ANTIMICROBIAL ACTIVITY

BACKGROUND OF THE INVENTION a) Field of the Invention

This invention relates to antimicrobial agents, especially to antimicrobial agents capable of imparting excellent weatherability to resins, synthetic fibers or the like without impairing the safety and transparency of these materials. This invention is also concerned with resin compositions making use of the above antimicrobial agents and further with articles making use of these resin compositions.

b) Description of the Related Art

Traditionally, antimicrobial agents have been classified roughly into an inorganic type and an organic type. A problem associated with inorganic antimicrobial agents is that, when incorporated as additives in resins, synthetic resins, paints or the like, resulting products are deteriorated in physical properties such as transparency and mechanical strength although these products are good in heat resistance and weatherability. With respect to the safety of inorganic antimicrobial agents, on the other hand, their effects on the ecosystem due to accumulation of metals such as silver as a result of future mass consumption are of concern because these antimicrobial agents contain metal ions such as silver ions.

A problem associated with organic antimicrobial agents, on the other hand, is that when incorporated as additives in resins, synthetic fibers, paints or the like, resulting products are accompanied by drawbacks in heat resistance and weatherability although these products are good in mechanical strength. Depending on the kinds of organic antimicrobial agents employed, a problem with respect to the transparency of resulting products may also arise.

SUMMARY OF THE INVENTION

An object of the present invention is to overcome the above-described problems and hence to provide an antimicrobial agent which, when incorporated as additives in resins, synthetic fibers or the like, can impart excellent weatherability and deterioration resistance to resulting products without impairing the transparency and safety of these materials.

As a result of extensive research, the present inventors have found that a 2,2,6,6-tetramethyl-4-piperidine derivative, when added to resins, synthetic fibers or the like, can impart stable antimicrobial activity and excellent weatherability and deterioration resistance to these materials without impairing their transparency and safety, leading to the completion of the present invention.

To achieve the above object, the present invention provides an antimicrobial agent comprising a 2,2,6,6-tetramethyl-4-piperidine derivative, an antimicrobial resin composition comprising the antimicrobial agent, and an antimicrobial article comprising the antimicrobial resin composition.

The antimicrobial agent according to the present invention can impart not only excellent antimicrobial activity but also superb heat resistance, weatherability and deterioration resistance to resins, synthetic fibers or the like without imparting the safety and transparency of these materials. Further, the resin composition making use of the antimicrobial agent and the article made of the resin composition have the above-described outstanding properties.

DETAILED DESCRIPTION OF THE INVENTION AND PREFERRED EMBODIMENTS

The present invention will next be described in further detail on the basis of preferred embodiments. 2,2,6,6-Tetramethyl-4-piperidine derivatives useful in the practice of the present invention are compounds having the following structure in their molecules.

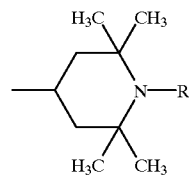

wherein R represents a hydrogen atom or an alkyl group.

As 2,2,6,6-tetramethyl-4-piperidine derivatives for use in the present invention, known compounds can be employed. Particularly preferred are the following compounds (a)–(e):

(a) Bis(2,2,6,6-tetramethyl-4-piperidyl)sebacate (a)

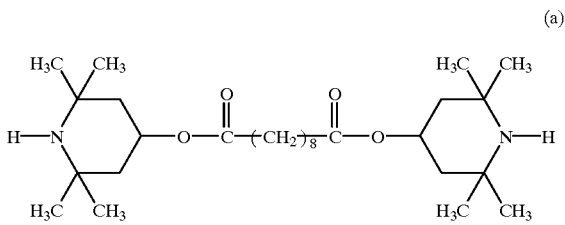

(b) Poly[{6-(1,1,3,3-tetramethylbutyl)amino-1,3,5-triazin-2,4-diyl}{(2,2,6,6-tetramethyl-4-piperidyl)imino}hexamethylene{(2,2,6,6-tetramethyl-4-piperidyl)imino}]

(b)

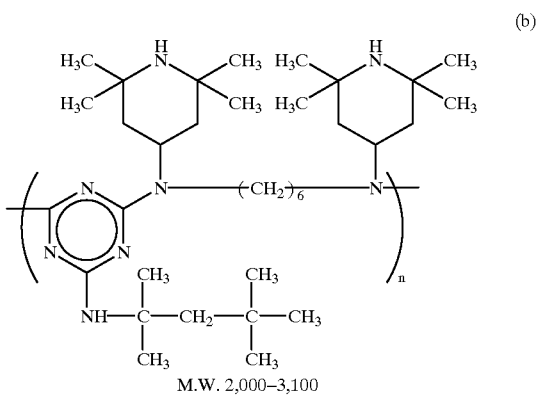

M.W. 2,000–3,100

(c) A mixed ester of 1,2,3,4-butanetetracarboxylic acid with 2,2,6,6-tetramethyl-4-piperidinol) and 3,9-bis(2-hydroxy-1,1-dimethylethyl)-2,4,8,10-tetraoxaspiro[5.5]-udecane

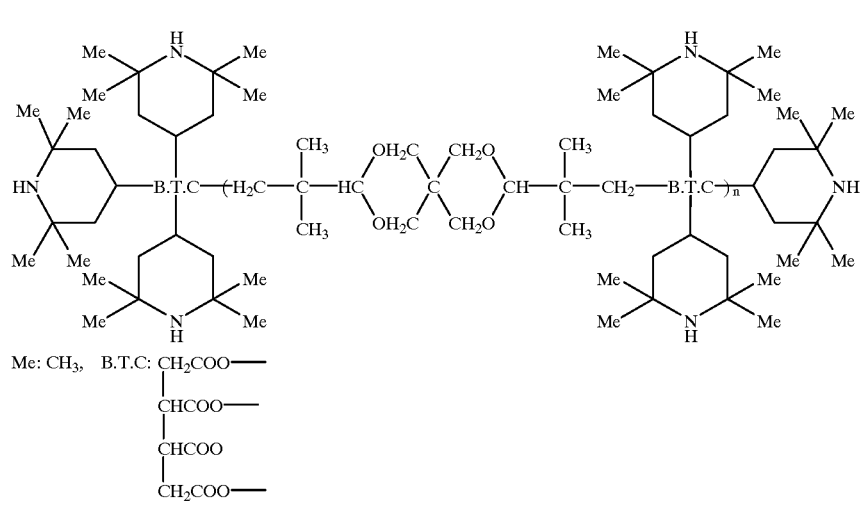
(c)

(d) Tetrakis(1,2,2,6,6-pentamethyl-4-piperidyl)-1,2,3,4-butanetetracarboxylate

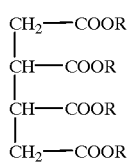 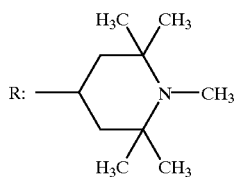
(d)

(e) Tetrakis(2,2,6,6-tetramethyl-4-piperidyl)-1,2,3,4-butanetetracarboxylate

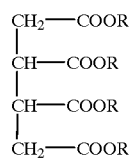 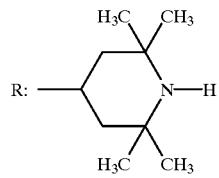
(e)

Among the above compounds, the compounds (a) and (b) are especially good in safety because they are described in the Positive List of Japan Hygienic Olefin and Styrene Plastics Association (JHOSPA) and their use in food containers and packages is permitted. These compounds can be used either singly or in combination.

The 2,2,6,6-tetramethyl-4-piperidine derivatives useful in the practice of the present invention have melting points or softening points in a range of from 80 to 135° C. and have excellent dispersibility in resins, so that they can provide antimicrobial resin compositions having high transparency.

The 2,2,6,6-tetramethyl-4-piperidine derivatives useful in the practice of the present invention are known to impart weatherability and deterioration resistance especially to resins, and can hence provide superior antimicrobial resin compositions to conventional organic antimicrobial agents.

The antimicrobial activity of each antimicrobial agent according to the present invention appears to be developed through a mechanism to be described next. Namely, the 2,2,6,6-tetramethyl-4-piperidine structure is believed to form a quaternary ammonium salt, which is considered to induce injuries of cell membranes and walls of microorganisms and denaturation and/or respiratory inhibition of zymoproteins, thereby presumably exhibiting antimicrobial activity.

No particular limitation is imposed on the resin to be used in the antimicrobial resin composition according to the present invention. Illustrative usable resins can include polyethylene resins, polypropylene resins, polyester resins, polystyrene resins, polyvinyl chloride resins, polyurethane resins, polyacrylic resins, polyamide resins, polyvinyl alcohol resins, and cellulose resins.

No particular limitation is imposed on the amount of the 2,2,6,6-tetramethyl-4-piperidine derivative to be used in the antimicrobial resin composition according to the present invention. Its preferred amount may however range from 0.05 to 5 parts by weight per 100 parts by weight of the resin. An amount of the 2,2,6,6-tetramethyl-4-piperidine derivative smaller than 0.05 part by weight leads to low antimicrobial effect, so that in the case of bis(2,2,6,6-tetramethyl-4-piperidyl)sebacate, antimicrobial effect can hardly be observed against Gram-negative bacteria. On the other hand, an amount of the 2,2,6,6-tetramethyl-4-piperidine derivative greater than 5 parts by weight involves a potential problem that physical properties of the resulting resin composition may be adversely affected.

Pigments, resin additives, other antimicrobial agents and/or the like can be added in the antimicrobial resin composition according to the present invention to such extents as not impairing the advantageous effects of the present invention. No particular limitation is imposed on the article having antimicrobial activity according to the present invention insofar as it is made of the antimicrobial resin composition according to the present invention. As illustrative examples, however, the following articles may be mentioned.

(1) Molded or otherwise formed, antimicrobial articles:

Articles obtained by molding or otherwise forming antimicrobial resin compositions of the invention by injection molding, extrusion, blow molding or the like. More specific examples can include food containers, waste or rubbish receptacles, stationery, housings of electric or electronic appliances, cosmetic containers, vehicle interior parts, kitchen utensils, bathroom utensils, and clothing storage containers.

(2) Antimicrobial fibers:

Articles obtained by forming the antimicrobial resin compositions of the present invention into fibers by spinning or the like, and those obtained by forming such fibers into woven fabrics or nonwoven fabrics. More specific examples can include clothing and carpets.

(3) Antimicrobial paints:

The antimicrobial resin compositions according to the present invention can be formulated into paints by using solvents or the like.

The present invention will hereinafter be described in detail on the basis of Examples and Comparative Examples, in which all designations of "part" or "parts" are by weight basis unless otherwise specifically indicated.

The following antimicrobial agents were employed in the Examples:

Antimicrobial agent a:
Bis(2,2,6,6-tetramethyl-4-piperidyl)sepacate (CAS No. 52829-07-9).

Antimicrobial agent b:
Poly[{6-(1,1,3,3-tetramethylbutyl)amino-1,3,5-triazin-2,4-diyl}{(2,2,6,6-tetramethyl-4-piperidyl)imino}hexamethylene{(2,2,6,6-tetramethyl-4-piperidyl)imino}] (CAS No. 71878-19-8).

Antimicrobial agent c:
A mixed ester of 1,2,3,4-butanetetracarboxylic acid with 2,2,6,6-tetramethyl-4-piperidinol and 3,9-bis(2-hydroxy-1,1-dimethylethyl)-2,4,8,10-tetraoxaspiro[5.5]undecane (CAS No. 119524-47-9).

Antimicrobial agent d:
Tetrakis(1,2,2,6,6-pentamethyl-4-piperidyl)-1,2,3,4-butanetetracarboxylate (CAS No. 91788-83-9).

Antimicrobial agent e:
Tetrakis(2,2,6,6-tetramethyl-4-piperidyl)-1,2,3,4-butanetetracarboxylate (CAS No. 64022-61-3).

EXAMPLE 1

A cell suspension, which had been subjected to preculture at 37° C. for 16 hours on a nutrient broth medium, were diluted 200-fold to obtain an inoculating cell suspension. The antimicrobial agent a was added at 500 ppm to the inoculating cell suspension. 5-ml Aliquots of the inoculating cell suspension were then placed in sterilized L-tubes, followed by incubation at 37° C. for 24 hours. The viable cell count of the cultured liquid medium was determined by the agar plate dilution method (shaker flask method). Antimicrobial activity tests were conducted using *Escherichia coli* and *Staphylococcus aureus*. The results are presented in Table 1.

EXAMPLES 2–5

Antimicrobial tests were conducted in a similar manner as in Example 1 except that the antimicrobial agents b to e were used in place of the antimicrobial agent a. The results are presented in Table 1.

COMPARATIVE EXAMPLE 1

Antimicrobial activity tests were conducted in a similar manner as in Example 1 except for the omission of the antimicrobial agent. The results are presented in Table 1.

TABLE 1

Results (Examples 1–5 & Comparative Example 1)

| | | *Escherichia coli* | | *Staphylococcus aureus* | |
|---|---|---|---|---|---|
| | Antimicrobial agent | Viable cell count (cells/m) | Inhibition (%) | Viable cell count (cells/m) | Inhibition (%) |
| Inoculating cell suspension | — | $1.0 \times 10^7$ | — | $4.9 \times 10^6$ | — |
| Example 1 | a | $2.1 \times 10^7$ | 99 | $<10^3$ | >99.9999 |
| Example 2 | b | $<10^3$ | >99.9999 | $<10^3$ | >99.9999 |
| Example 3 | c | $<10^3$ | >99.9999 | $<10^3$ | >99.9999 |
| Example 4 | d | $<10^3$ | >99.9999 | $<10^3$ | >99.9999 |
| Example 5 | e | $<10^3$ | >99.9999 | $<10^3$ | >99.9999 |
| Comp. Ex. 1 | — | $1.9 \times 10^9$ | 0 | $1.3 \times 10^9$ | 0 |

EXAMPLE 6

A low-density polyethylene resin (100 parts) and the antimicrobial agent a (0.3 part) were kneaded under heat and then formed into a transparent sample film. Antimicrobial activity was tested in a similar manner as in Example 1 except that 1.0 g of the sample film was added instead of the addition of 500 ppm of the antimicrobial agent a.

Further, weatherability was also tested in accordance with JIS K7113. Described specifically, the sample film was punched in the No. 2 dumbbell size and then exposed for 500 hours under a sunshine weatherometer. The elongation at break of the test piece after the exposure was measured by a tensile tester. The results are presented in Table 2.

EXAMPLES 7–10

Antimicrobial activity tests were conducted in a similar manner as in Example 6 except that the antimicrobial agents b to e were used in place of the antimicrobial agent a. The results are presented in Table 2.

COMPARATIVE EXAMPLE 2

Antimicrobial activity tests were conducted in a similar manner as in Example 6 except for the omission of the antimicrobial agent. The results are presented in Table 2.

TABLE 2

Results (Examples 6–10 & Comparative Example 2)

| | | Escherichia coli | | Staphylococcus aureus | | |
|---|---|---|---|---|---|---|
| | Anti-microbial agent | Viable cell count (cells/m) | Inhibition (%) | Viable cell count (cells/m) | Inhibition (%) | Weather-ability |
| Inoculating cell suspension | — | $1.0 \times 10^7$ | — | $4.9 \times 10^6$ | — | — |
| Example 6 | a | $7.6 \times 10^6$ | 99.6 | $6.0 \times 10^3$ | >99.9995 | ≥500% |
| Example 7 | b | $<10^3$ | >99.9999 | $<10^3$ | >99.9999 | ≥500% |
| Example 8 | c | $<10^3$ | >99.9999 | $<10^3$ | >99.9999 | ≥500% |
| Example 9 | d | $<10^3$ | >99.9999 | $<10^3$ | >99.9999 | ≥500% |
| Example 10 | e | $<10^3$ | >99.9999 | $<10^3$ | >99.9999 | ≥500% |
| Comp. Ex. 2 | — | $1.9 \times 10^9$ | — | $1.3 \times 10^9$ | — | 30% |

EXAMPLE 11

A polypropylene resin (100 parts) and the antimicrobial agent a (0.5 part) were kneaded under heat and then formed into a transparent sample plate of 5 cm×5 cm. A cell suspension, which had been subjected to preculture at 37° C. for 16 hours on the nutrient broth medium, were diluted with a phosphate buffer to obtain an inoculating cell suspension. The inoculating cell suspension was dropped onto a surface of the sterilized sample plate at four corners and a diagonal center thereof in an amount of 0.1 ml per location. After the sample plate was incubated at 37° C. and 90% or higher relative humidity for 24 hours in a sterilized Petri dish, cells were washed off with the phosphate buffer, and the viable cell count was then determined by the agar plate dilution method (dropping method). Antimicrobial activity tests were conducted using *Escherichia coli* and *Staphylococcus aureus*. The results are presented in Table 3.

EXAMPLES 12–15

Antimicrobial activity tests were conducted in a similar manner as in Example 11 except that the antimicrobial agents b to e were used in place of the antimicrobial agent a. The results are presented in Table 3.

COMPARATIVE EXAMPLE 3

Antimicrobial activity tests were conducted in a similar manner as in Example 11 except for the omission of the antimicrobial agent. The results are presented in Table 3.

TABLE 3

Results (Examples 11–15 & Comparative Example 3)

| | | Escherichia coli | | Staphylococcus aureus | |
|---|---|---|---|---|---|
| | Anti-microbial agent | Viable cell count (cells/m) | Inhibition (%) | Viable cell count (cells/m) | Inhibition (%) |
| Inoculating cell suspension | — | $2.1 \times 10^5$ | — | $2.9 \times 10^5$ | — |
| Example 11 | a | $2.3 \times 10^3$ | 99.8 | $<10^2$ | >99.9 |
| Example 12 | b | $<10^2$ | >99.99 | $<10^2$ | >99.9 |
| Example 13 | c | $<10^2$ | >99.99 | $<10^2$ | >99.9 |
| Example 14 | d | $<10^2$ | >99.99 | $<10^2$ | >99.9 |
| Example 15 | e | $<10^2$ | >99.99 | $<10^2$ | >99.9 |
| Comp. Ex. 3 | — | $1.2 \times 10^6$ | 0 | $1.6 \times 10^5$ | 0 |

EXAMPLE 16

A saturated polyester (100 parts) and the antimicrobial agent a (0.3 part) were kneaded under heat and then spun into transparent sample fibers. In a sterilized vial, 0.4 g of the sample fibers was inoculated with 0.2 ml of a cell suspension which had been subjected to preculture at 37° C. for 16 hours on the nutrient broth medium and then to dilution. After the sample fibers were incubated at 37° C. for 18 hours, cells were washed off with a physiological saline, and the viable cell count was then determined by the agar plate dilution method. Antimicrobial activity tests were conducted using *Staphylococcus aureus* and *Klebsiella pneumoniae*. The results are presented in Table 4.

EXAMPLES 17–20

Antimicrobial activity tests were conducted in a similar manner as in Example 16 except that the antimicrobial agents b to e were used in place of the antimicrobial agent a. The results are presented in Table 4.

COMPARATIVE EXAMPLE 4

The saturated polyester was kneaded under heat and then spun into transparent sample fibers. In a sterilized vial, 0.4 g of the sample fibers was inoculated with 0.2 ml of a cell suspension which had been subjected to preculture at 37° C. for 16 hours on the nutrient broth medium and then to dilution. Immediately after the inoculation, the sample fibers were washed with the physiological saline to separate cells from the sample fibers, and the viable cell count was then determined as an initial value by the agar plate dilution method. Another 0.4 g portion of the sample fibers, which had been inoculated likewise, was incubated at 37° C. for 18 hours, from which cells were washed off with the physiological saline. The viable cell count was then determined by the agar plate dilution method. Antimicrobial activity tests were conducted using *Staphylococcus aureus* and *Klebsiella pneumoniae*. The results are presented in Table 4.

TABLE 4

Results (Examples 16–20 & Comparative Example 4)

| | | Staphylococcus aureus | | Klebsiella pneumoniae | |
|---|---|---|---|---|---|
| | Anti-microbial agent | Viable cell count (cells/m) | Inhibition (%) | Viable cell count (cells/m) | Inhibition (%) |
| Initial value | — | $1.2 \times 10^5$ | — | $1.3 \times 10^5$ | — |
| Example 16 | a | $<10^2$ | 99.99 | $<10^2$ | >99.9999 |

TABLE 4-continued

Results (Examples 16–20 & Comparative Example 4)

| | Anti-microbial agent | Staphylococcus aureus | | Klebsiella pneumoniae | |
|---|---|---|---|---|---|
| | | Viable cell count (cells/m) | Inhibition (%) | Viable cell count (cells/m) | Inhibition (%) |
| Example 17 | b | <$10^2$ | >99.99 | <$10^2$ | >99.9999 |
| Example 18 | c | <$10^2$ | >99.99 | <$10^2$ | >99.9999 |
| Example 19 | d | <$10^2$ | >99.99 | <$10^2$ | >99.9999 |
| Example 20 | e | <$10^2$ | >99.99 | <$10^2$ | >99.9999 |
| Comp. Ex. 4 | — | $5.3 \times 10^6$ | 0 | $1.2 \times 10^8$ | 0 |

EXAMPLE 21

The resin composition of Example 6 was kneaded under heat and then extruded into a plastic food tray. It was confirmed to have excellent antimicrobial activity.

This application claims the priority of Japanese Patent Application No. HEI 10-76209 filed Mar. 24, 1998, which is incorporated herein by reference.

What is claimed is:

1. A method of imparting antimicrobial activity to a resin, comprising:

combining a resin with an antimicrobially effective amount of a 2,2,6,6-tetramethyl-4-piperidine derivative.

2. The method of claim 1, wherein the 2,2,6,6-tetramethyl-4-piperidine derivative is the sole antimicrobial agent combined with the resin.

3. The method of claim 1, wherein the 2,2,6,6-tetramethyl-4-piperidine derivative contains a group represented by the formula:

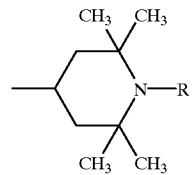

wherein R represents a hydrogen atom or an alkyl group.

4. The method of claim 1, wherein the 2,2,6,6-tetramethyl-4-piperidine derivative is selected from the group consisting of
  (a) bis(2,2,6,6-tetramethyl-4-piperidyl)sebacate,
  (b) poly[{6-(1,1,3,3-tetramethylbutyl)amino-1,3,5-triazin-2,4-diyl}{(2,2,6,6-tetramethyl-4-piperidyl)imino}hexamethylene{(2,2,6,6-tetramethyl-4-piperidyl)imino}],
  (c) a mixed ester of 1,2,3,4-butanetetracarboxylic acid with 2,2,6,6-tetramethyl-4-piperidinol and 3,9-bis(2-hydroxy-1,1-dimethylethyl)-2,4,8,10-tetraoxaspiro[5.5]-undecane,
  (d) tetrakis(1,2,2,6,6-pentamethyl4-piperidyl)1,2,3,4-butanetetracarboxylate, and
  (e) tetrakis(2,2,6,6-tetramethyl4-piperidyl)-1,2,3,4-butanetetracarboxylate.

5. The method of claim 4, wherein the 2,2,6,6-tetramethyl-4-piperidine derivative is (a).

6. The method of claim 4, wherein the 2,2,6,6-tetramethyl-4-piperidine derivative is (b).

7. The method of claim 4, wherein the 2,2,6,6-tetramethyl-4-piperidine derivative is (c).

8. The method of claim 4, wherein the 2,2,6,6-tetramethyl-4-piperidine derivative is (d).

9. The method of claim 4, wherein the 2,2,6,6-tetramethyl-4-piperidine derivative is (e).

10. The method of claim 1, wherein the resin is selected from the group consisting of polyethylene, polypropylene, polyester, polystyrene, polyvinyl chloride, polyurethane, polyacrylic, polyamide, polyvinyl alcohol and cellulose resins.

11. The method of claim 1, wherein 0.05 to 5 parts by weight of the 2,2,6,6-tetramethyl-4-piperidine derivative per 100 parts by weight of the resin are combined.

* * * * *